United States Patent
Tsubota et al.

(10) Patent No.: US 9,977,137 B2
(45) Date of Patent: May 22, 2018

(54) X-RAY IMAGE PICKUP DEVICE AND IMAGE RECONSTRUCTION METHOD

(71) Applicant: HITACHI, LTD., Tokyo (JP)

(72) Inventors: Yushi Tsubota, Tokyo (JP); Shinji Kurokawa, Tokyo (JP); Keisuke Yamakawa, Tokyo (JP); Yasutaka Konno, Tokyo (JP); Shinichi Kojima, Tokyo (JP); Fumito Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days. days.

(21) Appl. No.: 15/325,497

(22) PCT Filed: Jul. 23, 2015

(86) PCT No.: PCT/JP2015/071025
§ 371 (c)(1),
(2) Date: Jan. 11, 2017

(87) PCT Pub. No.: WO2016/017534
PCT Pub. Date: Feb. 4, 2016

(65) Prior Publication Data
US 2017/0176609 A1   Jun. 22, 2017

(30) Foreign Application Priority Data
Jul. 28, 2014   (JP) ................ 2014-152852

(51) Int. Cl.
*G06K 9/00*    (2006.01)
*G01T 1/29*    (2006.01)
(Continued)

(52) U.S. Cl.
CPC ............ *G01T 1/2985* (2013.01); *A61B 6/032* (2013.01); *A61B 6/4233* (2013.01); *G01N 23/046* (2013.01)

(58) Field of Classification Search
None
See application file for complete search history.

(56) References Cited

U.S. PATENT DOCUMENTS 4,637,040 A    1/1987    Sohval et al.
5,173,852 A    12/1992   Lonn
(Continued)

FOREIGN PATENT DOCUMENTS

JP    60-106439 A    6/1985
JP    04-231940 A    8/1992
(Continued)

OTHER PUBLICATIONS

International Search Report of PCT/JP2015/071025 dated Oct. 20, 2015.
(Continued)

*Primary Examiner* — Atiba O Fitzpatrick
(74) *Attorney, Agent, or Firm* — Mattingly & Malur, PC

(57) ABSTRACT

Provided is a technique in an X-ray imaging apparatus for implementing data interpolation approximating an ideal point response trajectory interpolation, along with reducing calculation load. A method is provided to perform interpolation at high speed, in a direction along the point response trajectory. Sinograms are interpolated in advance from measured data, as to representative angles (e.g., 0°, ±30°, ±60°, and 90°) only. When a pixel targeted for back projection is determined at the time of reconstruction, a slope of the point response trajectory is determined as to each view. According to the slope of the trajectory, each representative sinogram is added with weight, whereby interpolation data in association with any angle can be obtained.

8 Claims, 11 Drawing Sheets

(51) Int. Cl.
   A61B 6/03    (2006.01)
   G01N 23/04   (2018.01)
   A61B 6/00    (2006.01)

(56) References Cited

U.S. PATENT DOCUMENTS

| | | |
|---|---|---|
| 5,590,164 A | 12/1996 | Kawai et al. |
| 6,272,199 B1 | 8/2001 | Sembritzki et al. |
| 2005/0175141 A1 | 8/2005 | Bruder et al. |
| 2008/0095299 A1 | 4/2008 | Kohler et al. |
| 2010/0034344 A1 | 2/2010 | Hein et al. |
| 2011/0243298 A1 | 10/2011 | Miyazaki |
| 2013/0343508 A1 | 12/2013 | Hagiwara |

FOREIGN PATENT DOCUMENTS

| | | |
|---|---|---|
| JP | 08-010251 A | 1/1996 |
| JP | 2000-083942 A | 3/2000 |
| JP | 2000-139893 A | 5/2000 |
| JP | 2005-205218 A | 8/2005 |
| JP | 2007-529258 A | 10/2007 |
| JP | 2010-035812 A | 2/2010 |
| JP | 2011-229906 A | 11/2011 |
| JP | 2014-000349 A | 1/2014 |
| WO | 2011/018729 A1 | 2/2011 |

OTHER PUBLICATIONS

International Preliminary Report on Patentability received in corresponding International Application No. PCT/JP2015/071025 dated Feb. 9, 2017.

X-RAY IMAGE PICKUP DEVICE AND IMAGE RECONSTRUCTION METHOD

TECHNICAL FIELD

The present invention relates to an image reconstruction technique in an X-ray imaging apparatus.

BACKGROUND ART

An X-ray CT (Computed Tomography) apparatus is provided with an X-ray source for irradiating a subject with X-rays, and an X-ray detector for detecting X-rays passing through the subject, the X-ray detector being opposed to the X-ray source, and the X-ray CT apparatus reconstructs an image from variations of an X-ray attenuation factor inside the subject, by using a data processing system, on the basis of projection data in a plurality of directions, the projection data being obtained by rotational imaging around the subject. Typically, an X-ray tube is used as the X-ray source, which irradiates an electrode with electrons accelerated by high voltage, and generates X-rays by utilizing a bremsstrahlung process. In order to take an image of a wide range at once, the X-ray detector being frequently used, is provided with a two-dimensional array of X-ray detector elements, each made up of a combination of scintillator and photodiode.

Spatial resolution of an image obtained by the X-ray CT apparatus, depends on a focus size, the number of projection data items obtained per rotation, i.e., the number of views, and array density of the X-ray detector elements of the X-ray detector. If there is a need for improvement in any of those described above, a large amount of development costs are required.

Patent document 1 discloses FFS (Flying Focal Spot) technique, as a technique for enhancing spatial resolution of the X-ray CT apparatus. In the FFS technique, the focal spot is oscillated at high speed during rotational imaging, thereby doubling sampling density at the center of a scan field of view (SFOV).

In the FFS, the sampling density can be increased in the array direction (e.g., channel direction) of the sampling elements, which is a moving direction of the focal spot. However, the CT apparatus performs imaging by continuous rotation, and thus, it is not possible to obtain data items at two focal spots of the FFS, simultaneously at the same projection angle. Therefore, it is necessary to interpolate deficient data, in order to obtain data also in the view direction, with respect to each projection angle.

As one of data interpolation techniques in the X-ray CT apparatus, there is known an interpolation method that is used for rebinning data measured by a fan beam, so that the data is acquired just like measured by a parallel beam. It should be noted that conversion from the fan beam to the parallel beam is simply referred to as Fan-Para conversion. The patent document 2 describes one of the Fan-Para conversion techniques, which performs interpolation in the direction along a trajectory on a sinogram, depicted by the center of a display field of view (DFOV).

PRIOR ART DOCUMENT

Patent Document

Patent Document 1
WO2011/018729
Patent Document 2
Japanese Unexamined Patent Application Publication No. 2014-349

DISCLOSURE OF THE INVENTION

Problems to be Solved by the Invention

When a certain pixel on a tomographic image is considered, a position on a sinogram where the pixel position is projected moves along a view direction. A trajectory along which the position moves on the sinogram, i.e., the trajectory depicted on the sinogram (hereinafter, referred to as "point response trajectory") is different depending on the pixel position.

The interpolating method described in the patent document 2 performs interpolation along the point response trajectory of the center of a DFOV, and it is an ideal interpolation for the center of the DFOV. However, an optimum interpolation can be achieved only for the central region of the DFOV. On the other hand, when the point response trajectory is considered as to plural pixel positions, the point response trajectory varies depending on each pixel position, and therefore, it is not possible to interpolate the sinogram, only in one way. Theoretically, the interpolation being optimum for every pixel position can be implemented, by generating sinograms to which various interpolations have been applied, respectively for the pixel positions. However, there are at least a few hundreds to several tens of thousands of pixels, thus generating the corresponding number of sinograms may cause enormous calculation load, and it is impractical.

An object of the present invention is to provide an X-ray imaging apparatus that implements data interpolation approximating an ideal point response trajectory interpolation along with reducing calculation load, thereby enhancing a quality of image.

Means for Solving the Problems

The present invention employs a method that performs interpolation only at representative plural angle directions, so as to generate representative sinograms, and performs weighted averaging of the representative sinograms using weights which are different depending on reconstructed pixel positions when back projection is calculated.

The X-ray imaging apparatus of the present invention is provided with an X-ray source configured to generate X-rays from an X-ray focus, an X-ray detector having a two-dimensional array of plural detector elements, configured to detect X-rays emitted from the X-ray source and passing through a subject, a rotary mechanism configured to rotate the X-ray source and the X-ray detector which are opposed to each other, and an operation part configured to reconstruct a tomographic image of the subject, by using plural projection data items detected by the X-ray detector, according to emission of X-rays from the X-ray source along with rotating an emitting direction of the X-rays, wherein, the plural projection data items include a first sinogram where acquired data items are arranged, with the first axis representing detector element numbers in the rotation direction of the X-ray detector, and the second axis representing projection numbers respectively associated with rotation angles of the X-ray source, and the operation part is provided with a data interpolation part configured to interpolate the first sinogram, and an image reconstruction part configured to reconstruct an image by using a second sinogram that is generated by the data interpolation part, the data interpolation part performs interpolation along various angles θ, in making up for data deficiency included in the first sinogram or in rearranging the data items in the form suitable for a reconstruction process, so as to generate plural second sinograms, and the image reconstruction part performs an image reconstruction process including a process of weighted averaging of the plural second sinograms, using a weight corresponding to an angle difference between the angle θ and a slope of a trajectory on the second sinogram, depicted by a virtual point placed on the pixel position targeted for reconstruction.

The image reconstruction method of the present invention is for reconstructing a tomographic image of a subject, by using a first sinogram where acquired data items are arranged, with the first axis representing detector element numbers in a rotation direction of the X-ray detector, and a second axis representing projection numbers respectively associated with rotation angles of the X-ray source, the first sinogram being obtained by the X-ray imaging apparatus provided with a rotary mechanism of the X-ray source and the X-ray detector, and the method including a process of performing interpolation along plural different angles θ, when data deficiency included in the first sinogram is made up for, or the data items are rearranged in the form suitable for a reconstruction process, so as to generate plural second sinograms, wherein, the process includes weighted averaging of the plural second sinograms, using a weight corresponding to an angle difference between the angle θ and a slope of a trajectory on the second sinogram, depicted by a virtual point placed on the pixel position targeted for reconstruction.

Advantage of the Invention

According to the present invention, it is possible to implement data interpolation approximating an ideal point response trajectory interpolation, along with reducing calculation loads, and thereby enhancing an image quality.

BEST MODE FOR CARRYING OUT THE INVENTION

An X-ray imaging apparatus according to the present embodiments is provided with an X-ray source configured to generate X-rays from an X-ray focus, an X-ray detector having a two-dimensional array of plural detector elements, configured to detect X-rays emitted from the X-ray source and passing through a subject, a rotary mechanism configured to rotate the X-ray source and the X-ray detector which are opposed to each other, and an operation part configured to reconstruct a tomographic image of the subject, by using plural projection data items detected by the X-ray detector, according to rotary irradiation of the X-rays from the X-ray source.

The plural projection data items include a first sinogram where acquired data items are arranged, with the first axis representing detector element numbers in a rotation direction of the X-ray detector, and the second axis representing projection numbers respectively associated with rotation angles of the X-ray source. The operation part is provided with a data interpolation part configured to interpolate the first sinogram, and an image reconstruction part configured to reconstruct an image by using a second sinogram that is generated by the data interpolation part. The data interpolation part performs interpolation along plural different angles θ and generates plural second sinograms, when making up for data deficiency included in the first sinogram, or the data items are rearranged in the form suitable for a reconstruction process. The image reconstruction part performs an image reconstruction process including a process of weighted averaging of the plural second sinograms, using a weight corresponding to an angle difference between the angle θ and a slope of a trajectory on the second sinogram, depicted by a virtual point placed on the pixel position targeted for reconstruction.

It should be noted that a direction in which the data interpolation part performs interpolation (interpolation direction) is obtained as the following; a straight line at a predetermined angle passing through the deficient data in data space (sinogram) is conceived, and an angle (a direction) of the straight line is assumed as the interpolation direction on which data or data close thereto exists to be used for the interpolation, out of plural data items (undeficient data) positioned around the deficient data. However, this does not mean that data not on the straight line and data located relatively far from the straight line are eliminated from the data to be used in the interpolation process.

Figure 1:
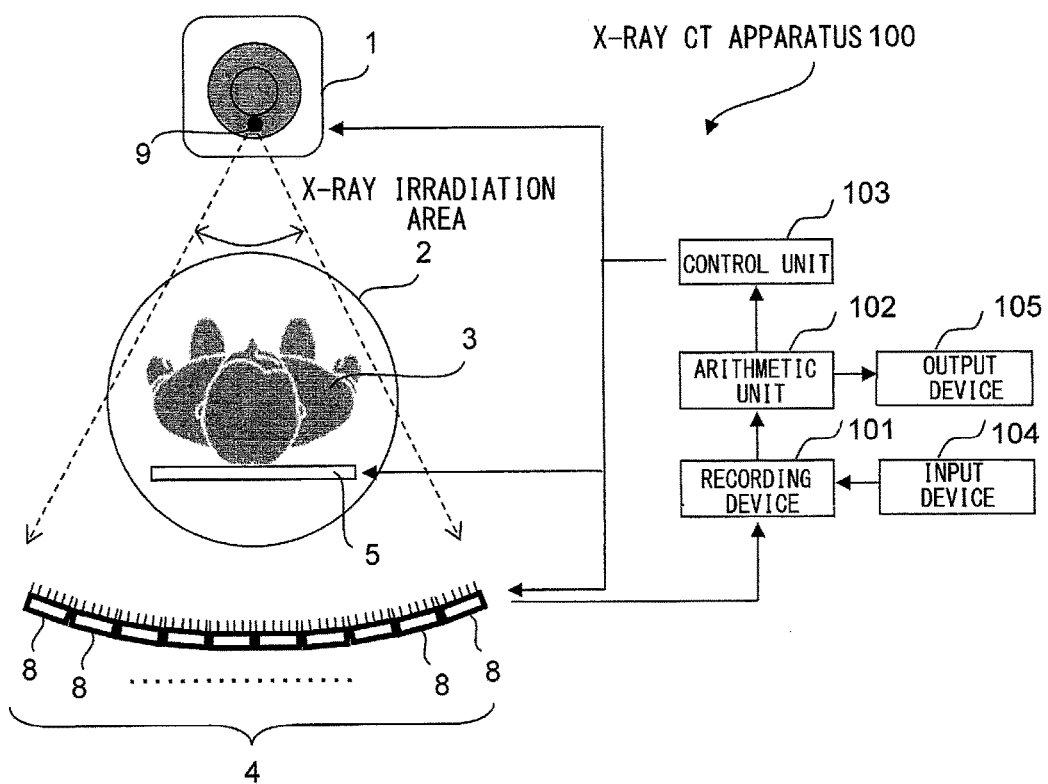
FIG. 1 illustrates an overall configuration of an X-ray CT apparatus to which the present invention is applied.

Embodiments of the X-ray imaging apparatus of the present invention will now be described, with reference to the accompanying drawings. FIG. 1 illustrates an overview of the X-ray CT apparatus 100 according to the present embodiment. This figure shows a structure of an imager, as an illustration viewed from a body axis direction of a subject 3 being a test object, and shows control and computing sections (referred to as a control system) in the form of a block diagram.

The imager is provided with a gantry, not illustrated, and the gantry has an opening 2 allowing the subject 3 to be placed in a central region thereof, and accommodates a scanner (rotary mechanism) having a rotating panel and a drive mechanism thereof. The rotating panel is supported by the gantry rotatably, configuring the center of the opening 2 as a rotation axis, and is provided with an X-ray tube 1 serving as the X-ray source, and an X-ray detector 4. A bed 5 is provided within the opening 2 in a movable manner, and the subject 3 is moved into the opening 2 in the state of being laid on the bed 5. This configuration enables rotational imaging of the subject 3 within the opening 2.

The X-ray source is provided with the X-ray tube 1 and a magnetic field (or electromagnetic field) generator for driving the X-ray tube 1, and X-rays are emitted from the X-ray focus 9 with a finite size, placed in the X-ray tube 1.

Figure 2:
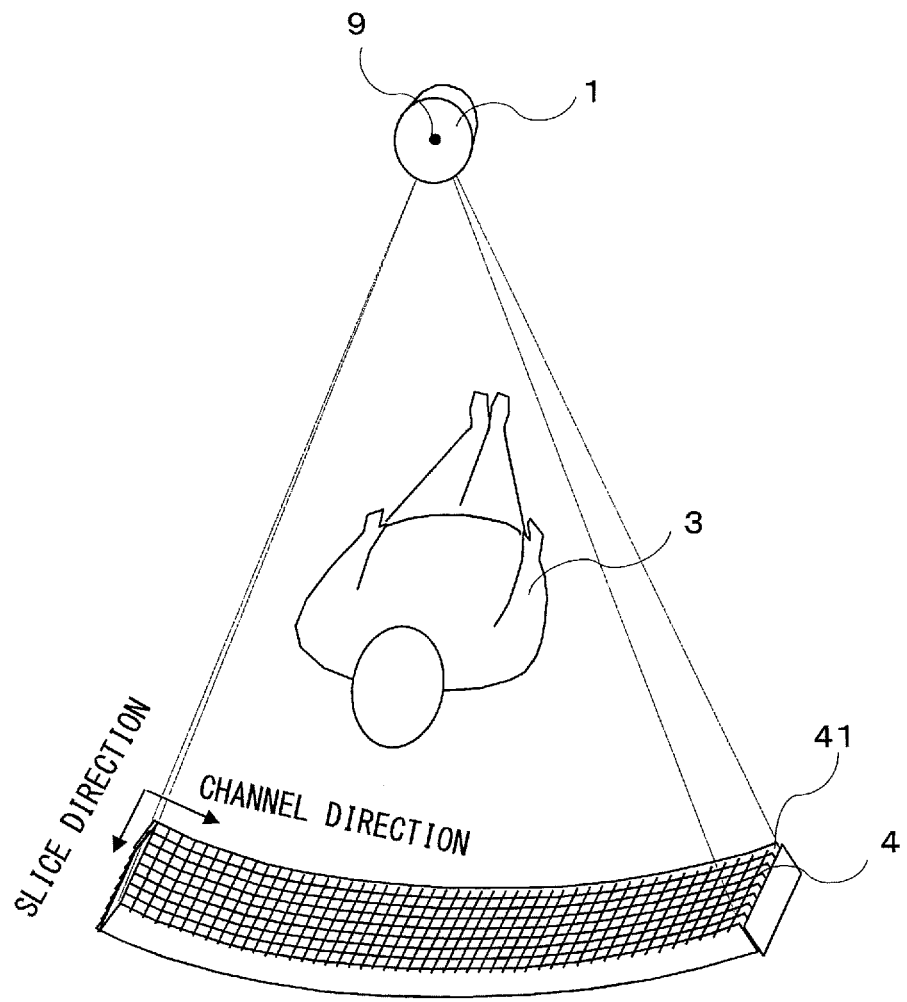
FIG. 2 illustrates one example of an array of X-ray elements in a detector module.

The X-ray detector 4 is disposed at a position opposed to the X-ray tube 1, placing the subject 3 therebetween. The X-ray detector 4 is divided into plural modules 8, and those detector modules 8 are arranged in an arc shape around the X-ray focus 9, or in the form of flat panel. As shown in FIG. 2, plural detector elements 41 are arranged in a two-dimensional array in the detector module 8. In this example, the direction of the array along the arc of the detector elements is referred to a channel direction, and the direction along the body axis of the subject 3 is referred to as a slice direction.

The control system comprises mainly, a recording device 101 such as a memory and a hard disk drive, an arithmetic unit (operation part) 102 such as a CPU (Central Processing Unit), a control unit (controller) 103, an input device 104 such as a mouse and a keyboard, and an output device 105 such as a monitor and a printer. The output device 105 may configure a GUI (Graphical User Interface), being combined with the input device 104.

The recording device 101 stores data obtained by imaging, data in the course of calculation by the arithmetic unit 102, parameters and numerical values necessary for the operations in the arithmetic unit 102, and further programs for activating the arithmetic unit 102 and the control unit 103.

The arithmetic unit 102 performs operations such as data correction and interpolation, in addition to the operations for image reconstruction, such as projection and back projection.

The control unit 103 performs control of the operations in all over the apparatus, such as control of a scanner, control of the operations of the X-ray tube 1 and the X-ray detector 4, and control of the bed 5 on which the test subject 3 is laid. By way of example, when the X-ray source has a function to oscillate the focal spot of the X-ray tube 1, the control unit performs control for oscillating the focal spot along with the rotational imaging.

Imaging by the X-ray CT apparatus 100 is performed under the control of the control unit 103, on the basis of scanning conditions configured by a user via the input device 104. A large number of projection data items obtained by the rotational imaging (data detected by the X-ray detector 4) are recorded in the recording device 101, then, the arithmetic unit 102 executes image processing operations, and the output device 105 such as a monitor displays information including a tomographic image of the subject 3.

Figure 3:
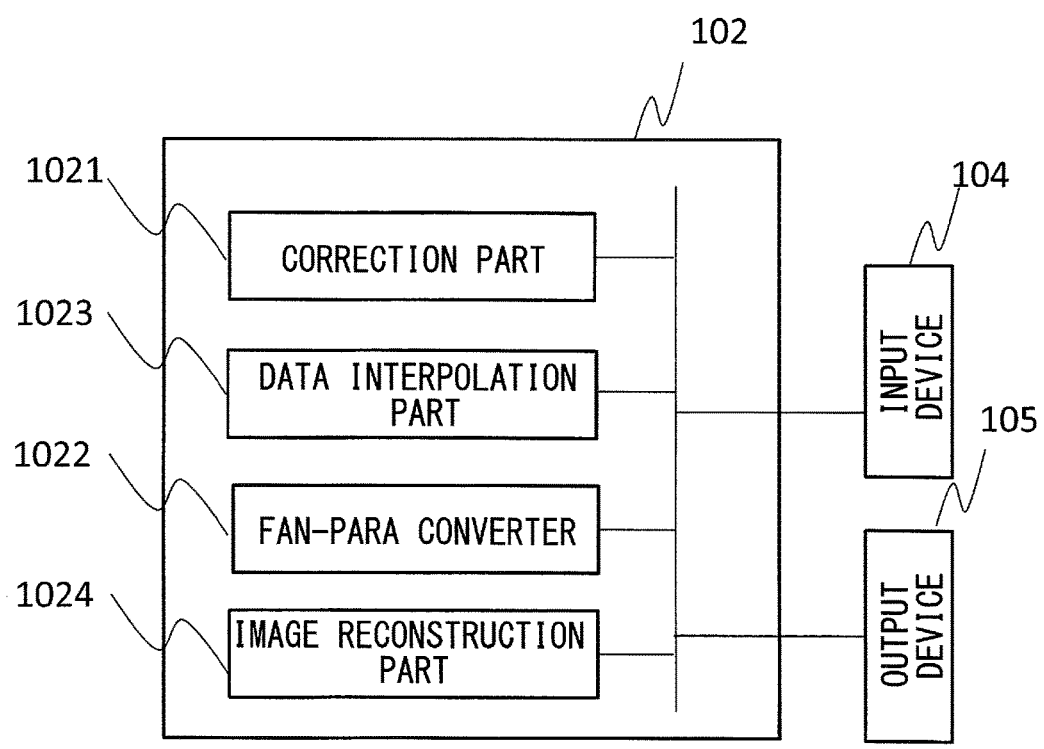
FIG. 3 is a functional block diagram illustrating an arithmetic unit of the X-ray CT apparatus as shown in FIG. 1.

The X-ray CT apparatus of the present embodiment is marked by features of the arithmetic unit 102, specifically, a feature of data interpolation process when deficient data is detected. FIG. 3 shows one example of a functional block diagram of the arithmetic unit 102 having this feature of data interpolation process.

As shown in FIG. 3, the arithmetic unit 102 includes a correction part 1021 configured to perform corrections on measured data, such as offset correction, sensitivity correction, scattered radiation correction, and beam hardening correction, a fan-para converter 1022 configured to convert measured data into virtual parallel beam data, when the measured data is fan-beam data, a data interpolation part 1023 configured to interpolate a deficient portion of the measured data (referred to as deficient data), and an image reconstruction part 1024 configured to reconstruct a CT image by using the data after interpolation. Some or all of the functions in the above-mentioned parts are implemented, when programs stored in advance in the recording device 101 are loaded on the CPU and executed. In some cases, a part of the functions may be implemented by ASIC (Application Specific Integrated Circuit) or FPGA (Field-Programmable Gate Array).

Prior to describing specific processing details and procedures of the arithmetic unit 102, data including deficiency will be explained, taking an FFS imaging as a typical example.

Figure 4:
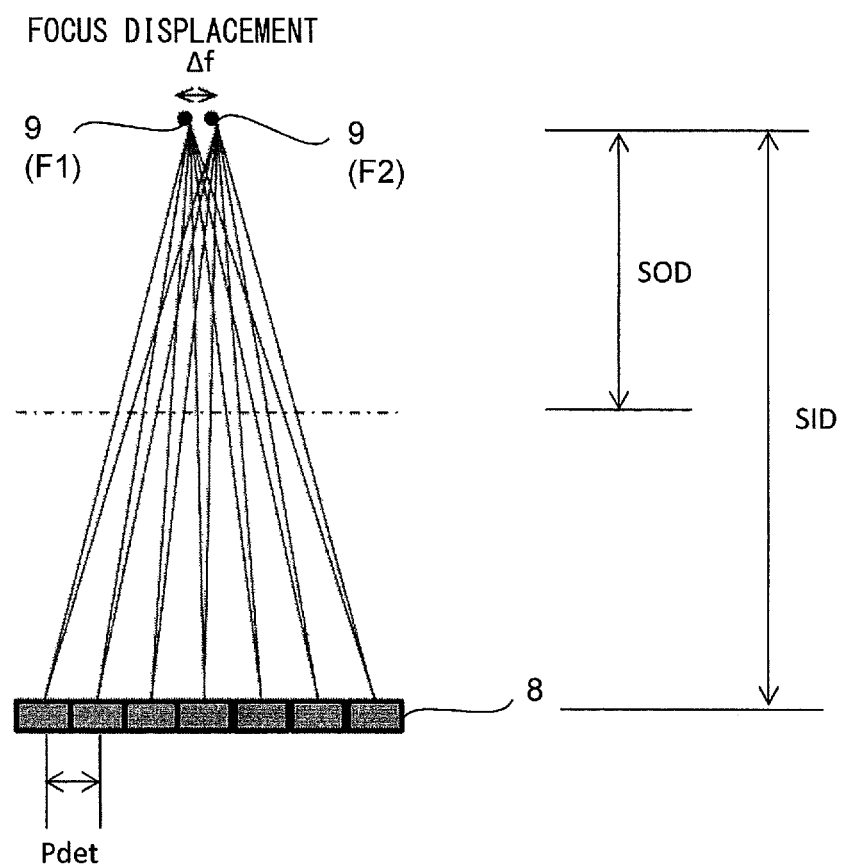
FIG. 4 illustrates an FFS imaging in the X-ray CT apparatus as shown in FIG. 1.

FIG. 4 is a conceptual diagram showing double density sampling according to the FFS. In the FFS imaging, a magnetic field (or electromagnetic field) generator provided in the X-ray tube 1 is used to deflect a trajectory of electron beam, thereby displacing a position of the X-ray focus 9, with respect to each projection (view). The focus may be displaced in a gantry rotation direction (channel direction) or in a body axis direction (slice direction). For ease of explanation, FIG. 4 illustrates the case where the focus 9 is displaced between the two points F1 and F2 in the channel direction. Also in the following, the case of displacement in the channel direction will be described, but it should be noted that the present invention is not limited to this focus displacement method.

As shown in FIG. 4, according to the focus displacement, density of the line segments connecting the X-rays and the centers of the detector elements is doubled, around the middle position of the scan field of view (a plane indicated by a dashed-dotted line).

Movement Δf of a focal central position (average position during one projection) for achieving the double density follows the formula 1, where "$p_{det}$" is a detector element pitch in the focus displacement direction, "SOD" is distance between the X-ray focus 9 and the center of gantry rotation, and "SID" is distance between the X-ray focus 9 and the detector module 8 (the same shall apply hereinafter).

[Formula 1]

$$\Delta f = \frac{p_{det}}{2}\left(\frac{SOD}{SID-SOD}\right) \quad (1)$$

Figure 5:
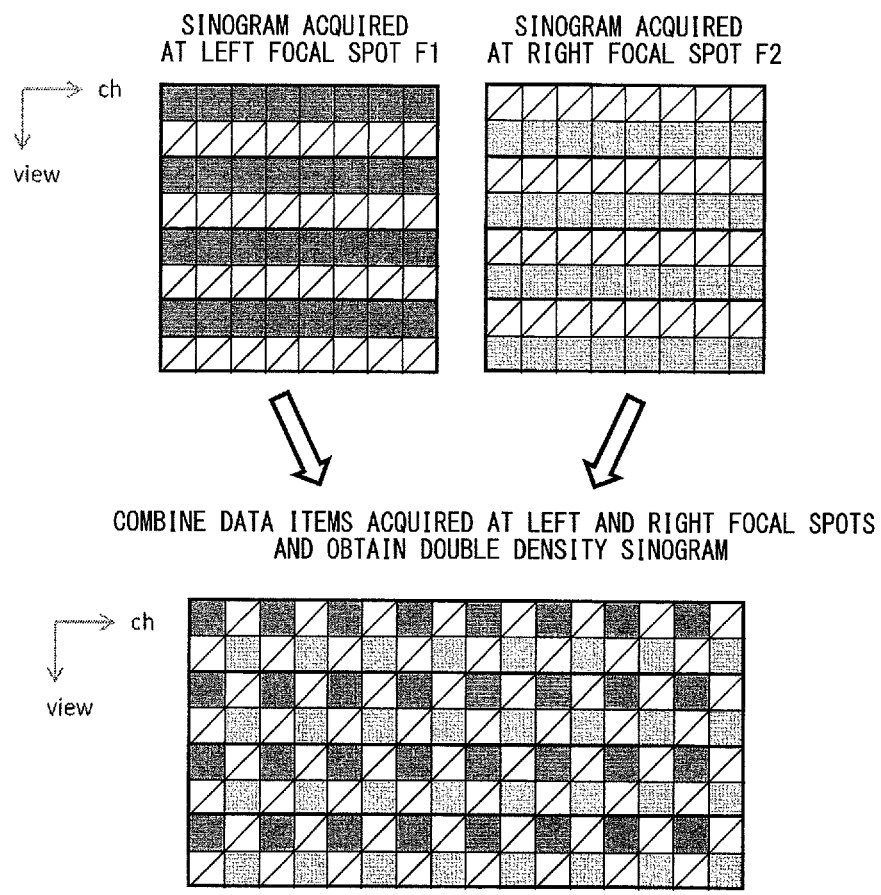
FIG. 5 illustrates data (first sinogram) obtained by the FFS imaging, and deficient data.

Under the conditions above, if rotational imaging is performed continuously while displacing the focus in the channel direction, the focal spots are switched between the adjacent projection angles, and therefore, data items of both focal spots cannot be obtained simultaneously at the same projection angle. Therefore, as shown in FIG. 5, the sinogram (first sinogram) obtained by executing the FFS, includes deficient data items that exist in every other line in each of the channel direction and the view direction. In FIG. 5, a voxel with a slash represents the deficient data.

The simplest method for interpolating the deficient data is linear interpolation in the channel direction (channel interpolation) or linear interpolation in the view direction (view interpolation). When comparison is made between the case where the channel interpolation is applied uniformly to the sinogram and the case where the view interpolation is applied uniformly thereto, the view interpolation is superior in spatial resolution on the middle position of the scan field of view (SFOV), whereas the channel interpolation is superior in spatial resolution in the surroundings of the scan field of view. This is because, a large part of the point response trajectory at the middle position of the scan field of view goes along the view direction, whereas a large part of the point response trajectory at the position surrounding the scan field of view goes along the channel direction.

Figure 6:
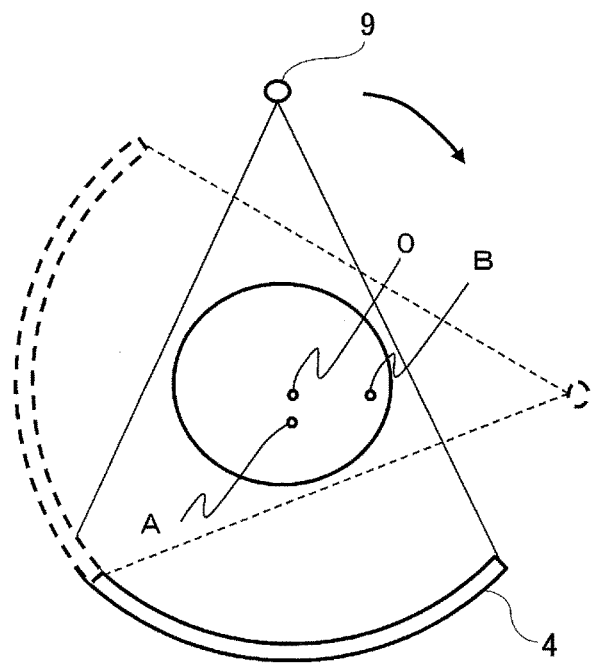
FIG. 6 illustrates a trajectory of a predetermined pixel on the sinogram.
Figure 6:
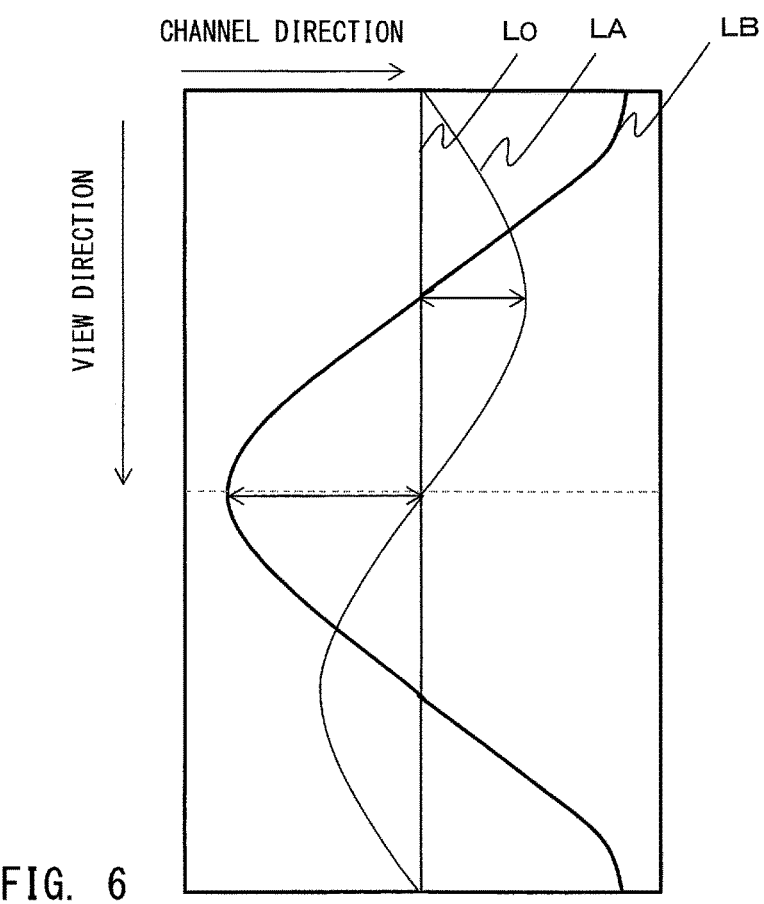

Considering the characteristics above, it is conceived that an optimum interpolation method is to perform interpolation in the direction along the point response trajectory depicted by each pixel on the sinogram (hereinafter, referred to as trajectory interpolation). FIG. 6 illustrates a concept of the trajectory interpolation. FIG. 6 shows the point response trajectories LO, LA, and LB on the sinogram shown on the lower side of the figure, respectively for the three positions O, A, and B in the SFOV shown on the upper side. As illustrated, the point response trajectory at the central position O of the scan field of view becomes the straight line LO passing through the center of the channel direction, in parallel with the view direction. At the positions other than the center, the trajectories become almost sine curves (somewhat distorted sine curves in the case of fan beams), having an amplitude corresponding to the displacement from the center position. The trajectory interpolation performs interpolation of data, assuming the direction along this point response trajectory as the interpolating direction, and it is an ideal interpolation for the pixel at the position that depicts the point response trajectory. As seen from FIG. 6, however, the point response trajectories of the respective pixels on the sinogram are overlapping one on another, it is not possible to perform interpolation assuming the sinogram as only one type.

According to the present embodiment, a plurality of sinograms (second sinograms, hereinafter referred to as representative sinograms) are generated, which are interpolated in various interpolation directions. Those plural representative sinograms are weighted variously on the pixel position basis, and used for image reconstruction (back projection). Accordingly, it is possible to obtain an image superior in overall image quality along with reducing calculation load, without deteriorating spatial resolution that depends on the pixel position. Various methods can be employed for configuring the representative sinograms, from viewpoints of reduction of calculation load and enhancement of image quality (in particular, enhancement of spatial resolution). Embodiments of the operation of the arithmetic unit 102 will now be described in the following.

First Embodiment

Figure 7:
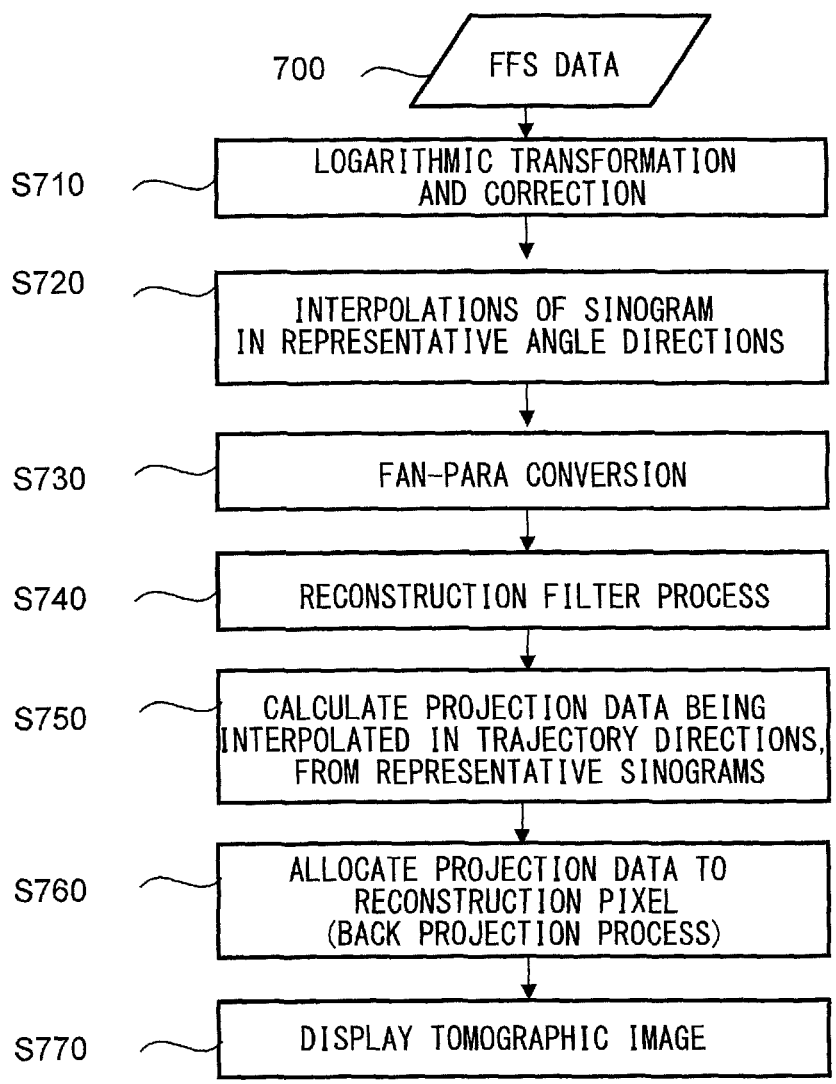
FIG. 7 is a flowchart showing an operational procedure of the operation part according to the first embodiment.

In the first embodiment, data interpolation is performed at a predetermined representative angle. FIG. 7 shows a processing flowchart of the arithmetic unit 102 according to the present embodiment. In here, a filtered back projection method will be described as an example of the reconstruction method.

Firstly, the correction part 1021 applies to the data obtained by the FFS measurement (700), already known corrections, such as a logarithmic transformation, offset correction and sensitivity correction of the detector elements, X-ray intensity correction, scattered radiation correction, and beam hardening correction (S710).

Next, assuming the view direction as an axis on the sinogram, the data interpolation part 1023 determines representative angles θi (more than one) with respect the axis, and performs interpolation in each direction, as to each of the representative angles (S720). The representative angle Gi is configured on the basis of a predetermined angle increment, setting 90 degrees (absolute value) as a maximum, for instance. For example, the increment of the angle is set as 30 degrees, and seven angles θi=−90°, −60°, −30°, 0°, 30°, 60°, and 90° are configured as the representative angles. The subscript i of θ indicates a serial number given to the representative angles, in the ascending order of the angles. It should be noted that the representative angles are not necessarily incremented at regular intervals.

Interpolation in a specific angle direction means that the interpolation is performed by using data items (undeficient data) arranged along the angle direction.

Figure 8:
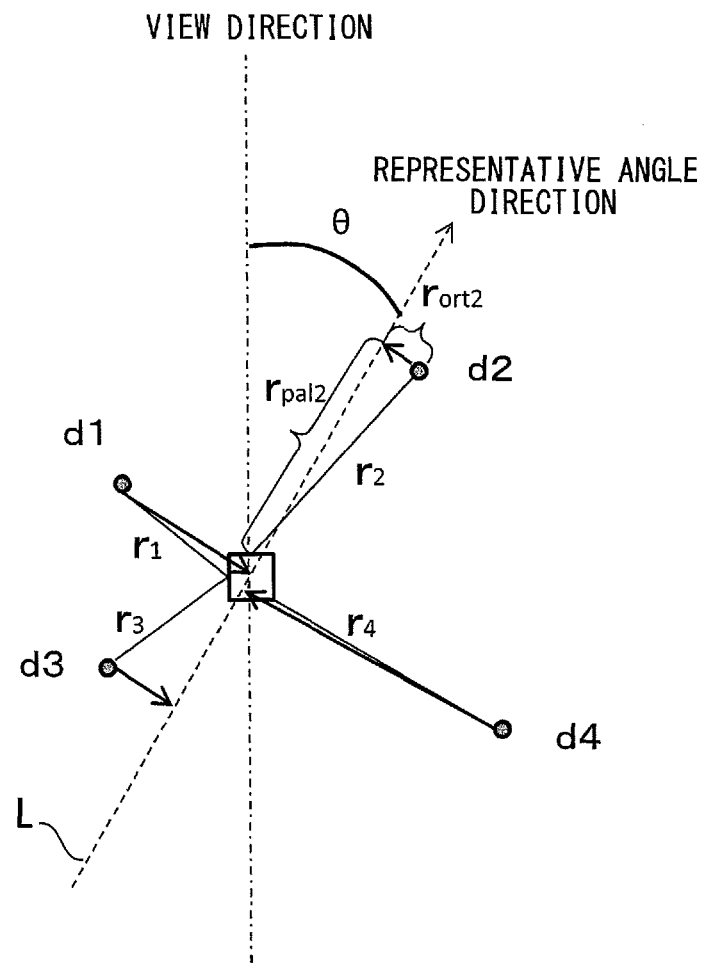
FIG. 8 illustrates interpolation of the deficient data.

With reference to FIG. 8, an explanation will be provided. In FIG. 8, a deficient position is indicated by a square, and the data items d1 to d4 around the square are indicated by circles. The sinogram data d is represented as a function of the detector element number in the channel direction "ch", the detector element in the slice direction "sl", and the projection number "view". Those variables are multiplied by appropriate coefficients α, β, and γ, and combined to be represented by vector x=(αch, βsl, γ view), and the deficient position on the sinogram is represented by x'. Then, the data being interpolated follows the formula 2, in general.

[Formula 2]

$$d(x') = \frac{\sum_{x} w(x - x') d(x)}{\sum_{x} w(x - x')} \quad (2)$$

In the formula 2, w(x−x') is a weight which is determined on the basis of the relationship between the deficient position x' and the vector x being a variable of the data d(x) for interpolating the deficient position. When distance r between the data items on the sinogram is defined by the formula 3 and the weight is defined as $w(r)=r^{-2}$, the interpolation is performed with increasing the weight of the data at the position closest to the deficient position x' (d1 in FIG. 8) in the formula 2, and the angle direction is not considered.

[Formula 3]

$$r = \sqrt{(x-x') \cdot (x-x')} \quad (3)$$

On the other hand, in the case of the interpolation in the angle direction indicated by the dotted line as shown in FIG. 8, the interpolation is performed, considering the distance from the straight line L passing through the deficient position and having the representative angle (the angle with respect to the axis in the view direction). Specifically, as to the data items in the neighborhood of the deficient position (d1 to d4 in FIG. 8), the shortest distance $r_{ort}$ to the straight line L is obtained, and it is defined as $w(r_{ort})=r_{ort}^{-2}$. In addition, distance $r_{pal}$ $(=(r^2-r_{ort}^2)^{1/2})$ parallel to the straight line L (in the representative angle direction) may also be obtained, and as shown in the formula 4, new distance r' is defined by combining $r_{ort}$ and $r_{pal}$ using an appropriate weight ε, so as to obtain $w(r')=r'^{-2}$.

[Formula 4]

$$r' = \sqrt{\frac{2\varepsilon}{1+\varepsilon}(r_{ort}^{2t}) + \frac{2}{1+\varepsilon}(r_{pal}^2)} \quad (4)$$

As shown in the formula 5, restraint may be provided so that data items located beyond a certain distance R are not used. This may prevent deterioration of resolution.

[Formula 5]

$$w(r') = \left\{\frac{\max(0, R - r')}{Rr'}\right\}^2 \quad (5)$$

The data interpolation part 1023 applies the interpolation as described above to all the deficient positions in the same angle direction, and obtains representative sinogram in this angle direction. Then, this interpolation process is performed as to all the angle directions being provided, and there are obtained the same number of representative sinograms (sinograms after interpolation) as the number of the angle directions being provided (representative angles).

Next, referring to FIG. 7 again, the fan-para converter 1022 and the image reconstruction part 1024 respectively apply a fan-para conversion (S730) and a reconstruction filtering process (S740) to each of the representative sinograms. The fan-para conversion is a process to convert the data obtained in the form of fan beams, into the data that is obtained on the assumption of parallel beam irradiation, and it is a type of interpolation process enabling a publicly known interpolation method, including interpolation that is weighted in accordance with distance, for instance. The reconstruction filtering process is a process that convolutes a reconstruction function into data, and any of publicly known reconstruction filters to be applied to the data, such as Ramachandran filter, Shepp filter, and Chesler filter, may be selected appropriately, considering a desired spatial resolution and contrast resolution. This selection of the reconstruction filter may be performed by a user via the input device 104, for instance, by choosing a type of the filter directly, or selecting a desired resolution.

FIG. 7 shows an example that the fan-para conversion (S730) is performed after generating the representative sinograms (S720), but those steps may be reversed. In other words, after applying the fan-para conversion to the corrected data, a plurality of representative sinograms in various interpolation directions may be generated. However, the procedure shown in FIG. 7 is preferable, so as not to deteriorate the resolution. Alternatively, generating the representative sinograms (S720) and the fan-para conversion (S730) may be performed simultaneously.

Then, back projection is performed by using the data of the sinograms (data with respect to each angle direction) to which the fan-para conversion and the reconstruction filtering process have been applied. For this purpose, first thing to do is to calculate from the representative sinograms, projection data after trajectory interpolation, which is to be used in the back projection process (S750).

Here, the sinograms after the process of S740 are represented by $D[\theta i]$ ($\theta i$ indicates the representative angle). $D[\theta i]$ is a function of the detector element number "CH" in the channel direction after the fan-para conversion, the detector element number "SL" in the slice direction after the fan-para conversion, and the projection number "VIEW" after the fan-para conversion.

When coordinates of the pixel targeted for the back projection are determined, the point response trajectory depicted on the sinogram is also determined accordingly. When this trajectory is expressed by f(VIEW), the angle $\Theta$ in the trajectory direction is represented by arctan [f'(VIEW)]. The sinogram data $D[\Theta]$ used in the back projection is obtained by the formula 6, using plural representative sinograms at the representative angles which are close to $\Theta$.

[Formula 6]

$$D[\Theta] = \frac{\sum_i g(\Theta - \theta_i) D[\theta_i]}{\sum_i g(\Theta - \theta_i)} \quad (6)$$

In the formula 6, g represents a weight being a function of the angle difference between $\Theta$ and $\theta_i$. That is, the smaller is the angle difference between $\theta_i$ and the angle $\Theta$ of the sinogram data $D[\Theta]$, the larger weight is provided. The representative sinogram data used in the calculation of the formula 6 may be only two representative angle data items satisfying $\theta_j \leq \Theta < \theta_{j+1}$. The weight in this situation may be expressed by the formula 7, using Kronecker delta symbol $\delta$, for instance.

[Formula 7]

$$g(|\Theta - \theta_i|) = \left(1 - \frac{|\Theta - \theta_j|}{|\theta_{j+1} - \theta_j|}\right)\delta_{ij} + \left(1 - \frac{|\Theta - \theta_{j+1}|}{|\theta_{j+1} - \theta_j|}\right)\delta_{i(j+1)} \quad (7)$$

Figure 9:
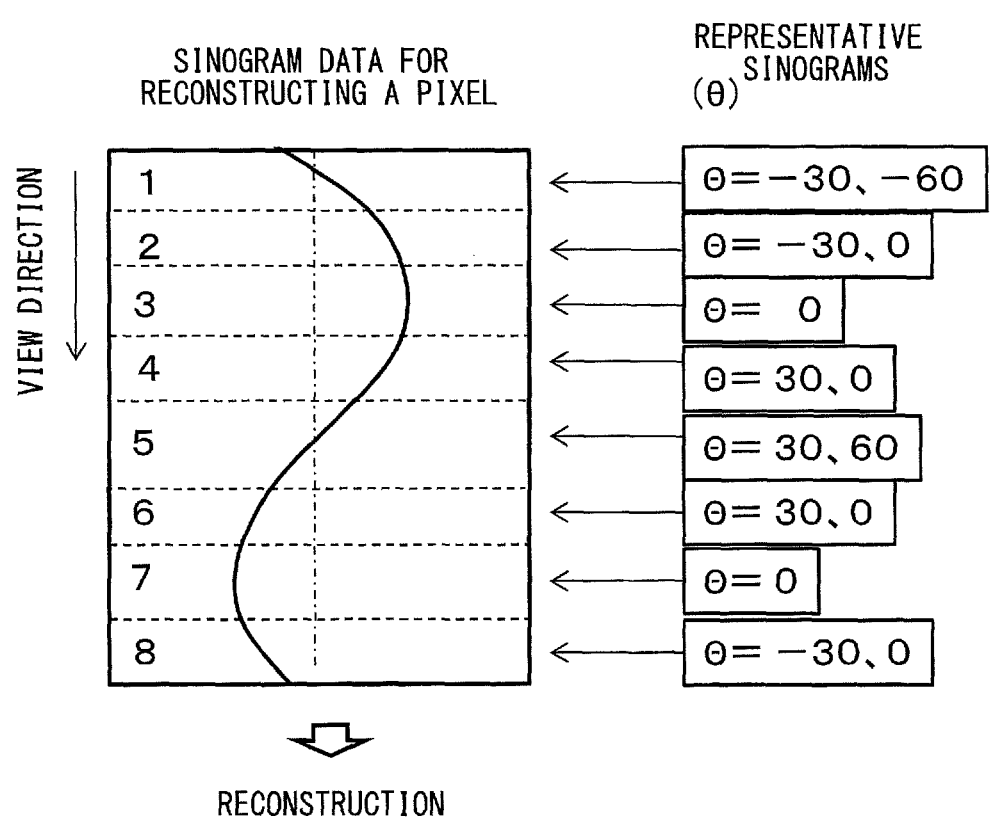
FIG. 9 illustrates a concept of an image reconstruction using plural representative sinograms (second sinograms)

The angle $\Theta$ in the trajectory direction varies along the point response trajectory f(VIEW) at the pixel other than the rotation center position, and therefore the calculation in the formula 6 above is carried out for every projection number (the view number after the fan-para conversion). FIG. 9 illustrates this situation. In accordance with the variations of the angle of the point response trajectory on the sinograms as shown on the right side of FIG. 9, a different combination of the representative sinograms is used. For example, in the region 1 where the absolute value of the angle of the point response trajectory is maximized (equal to or smaller than 60 degrees), a weight obtained by the formula 7 is applied, both to the representative sinogram interpolated by the interpolation method at −30 degrees and to the representative sinogram interpolated by the interpolation method at −60 degrees, and data is acquired accordingly. In the region 3, the point response trajectory is approximately parallel to the view direction, and thus the representative sinogram interpolated by the interpolation method at 0 degree is used.

Next, $D[\Theta]$ obtained by the formula 6 is back-projected to a certain pixel (S760). A method for calculating the back projection is generally known, and the calculation is performed according to the following method, for instance.

As to the back projection direction, a position where the coordinates of the pixel center are projected, on a parallelized virtual detector plane (a position of a virtual point placed on the pixel position that is required to be reconstructed) is represented by (CH', SL'). The above described $D[\Theta]$ is data that depends on (CH, SL), but CH and SL are discrete. Therefore, it is necessary to estimate the data (CH', SL') according to interpolation. The interpolation is performed according to the formula 8, by using an appropriate weight h associated with the distance between the data position to be interpolated and the data position to be used for the interpolation.

[Formula 8]

$$D[\Theta](CH', SL') = \frac{\sum_{CH,SL} h(\Delta CH, \Delta SL) D[\Theta](CH, SL)}{\sum_{CH,SL} h(\Delta CH, \Delta SL)} \quad (8)$$

In here, $\Delta CH = |CH' - CH|$ and $\Delta SL = |SL' - SL|$. In the formula 8, it is not necessary to perform interpolation along a specific direction, and already-known interpolation may be utilized such as spline interpolation. The interpolation according to the formula 6 and the formula 8 may be performed simultaneously. In this case, $D[\Theta]$ can be obtained according to the formula 9.

[Formula 9]

$$D[\Theta](CH', SL') = \frac{\sum_{i,CH,SL} h(\Delta CH, \Delta SL)g(\Theta - \theta_i)D[\theta_i](CH, SL)}{\sum_{i,CH,SL} h(\Delta CH, \Delta SL)g(\Theta - \theta_i)} \quad (9)$$

The process using the aforementioned formulas 6 and 8, or the formula 9, is applied to all the pixels and all the views, thereby obtaining a tomographic image of the subject. The tomographic image may be displayed on the output device 105 such as a monitor (S770).

According to the present embodiment, a plurality of representative sinograms in various interpolation directions are prepared, and at the time of back projection, the data of the representative sinograms are used, being weighted pixel by pixel considering the point response trajectory of each pixel. With this configuration, interpolation approximating the point response trajectory can be performed, thereby enhancing an image quality and achieving effective densification, in a technique such as the FFS which requires interpolation of deficient data.

It should be noted that the present embodiment can be applied not only to the FFS, but also to any other types of measurement, for the case where a deficiency occurs in data. For example, the present embodiment is also applicable when any of the detector elements in the X-ray detector 4 is faulty and the data in that detector element part is deficient.

In the description above, there are shown the example that the maximum value of the representative angle of the representative sinogram is +90 degrees and the minimum value is −90 degrees. However, the way how the representative sinograms are determined is not limited to the aforementioned embodiment, and various modifications are possible. Hereinafter, modification examples will be described, when the data interpolation part 1023 generates representative sinograms.

Modification Example 1

In the modification example 1, a maximum value and a minimum value of the representative angle are configured as values that satisfy a scan condition. As seen from FIG. 6, since the maximum value $\Theta_{max}$ of the slope of the point response trajectory never exceeds 90 degrees, the maximum value of the representative angle may be set to a value smaller than 90 degrees, in accordance with the scan condition. The maximum value $\Theta_{max}$ of the representative angle in accordance with the scan condition may be obtained according to the next formula 10. It should be noted that the minimum value is given as $-\Theta_{max}$.

[Formula 10]

$$\Theta_{max} = \arctan\left(\frac{2\pi}{VIEW_{max}} \frac{SID}{SOD} \frac{R_{DFOV}}{\Delta CH}\right) \quad (10)$$

In this formula, $VIEW_{max}$ is the number of VIEW counts per rotation, and $R_{DFOV}$ is a maximum radius of a pixel position included in the DFOV, when measurement is performed using cylindrical coordinates about the gantry rotation center. The aforementioned $R_{DFOV}$ may be a maximum radius $R_{ROI}$ of a pixel position included in any user-designated region of interest (ROI).

According to the modification example 1, unnecessary representative sinograms are not generated, and thereby further reducing the calculation load. If the number of the representative sinograms is the same, reduction of the increment of the angle may enhance a degree of approximation to the trajectory interpolation more, and higher precision is achieved in performing the interpolation.

Modification Example 2

In the modification example 1, the maximum value and the minimum value are changed in accordance with the scan condition. In the modification example 2, the increment of the representative angle is changed in accordance with a configuration of a reconstruction filter.

The reconstruction filter may be selected by a user, considering spatial resolution of an image, and the like. In this situation, when a low-resolution reconstruction filter is selected, the increment of the angle may be made larger, so as to reduce the number of the representative sinograms. On the other hand, when a high-resolution reconstruction filter is selected, the increment of the angle may be made smaller, thereby enhancing the precision of the trajectory interpolation.

Also in selecting a focus size, a rotation speed, a helical pitch, and smoothing intensity in an iterative reconstruction method, a function to automatically adjust the number of representative sinograms may be provided, in accordance with an image quality that is assumed as requested by the user. Similar to the description above, the adjustment is performed in such a manner that the higher is the requested spatial resolution, the larger number of the representative sinograms are prepared.

Modification Example 3

In the modification example 3, the interpolation method is simplified in such a manner that interpolation depends on only an absolute value of an interpolation angle. In other words, only either one of a positive angle and a negative angle (e.g., positive angle) is employed as the representative sinogram. In this case, the formula 11 is used instead of the formula 2.

[Formula 11]

$$d(ch', sl', view') = \quad (11)$$
$$\frac{d(ch', sl', view'-1) + d(ch', sl', view'+1)}{2}\cos^2\Theta +$$
$$\frac{d(ch'-1, sl', view') + d(ch'+1, sl', view')}{2}\sin^2\Theta.$$

Since the formula 11 produces the same result from any of $+\Theta$ and $-\Theta$, it is only required to generate a representative sinogram of the positive angle ($0 \le \theta \le \Theta max$).

Figure 10:
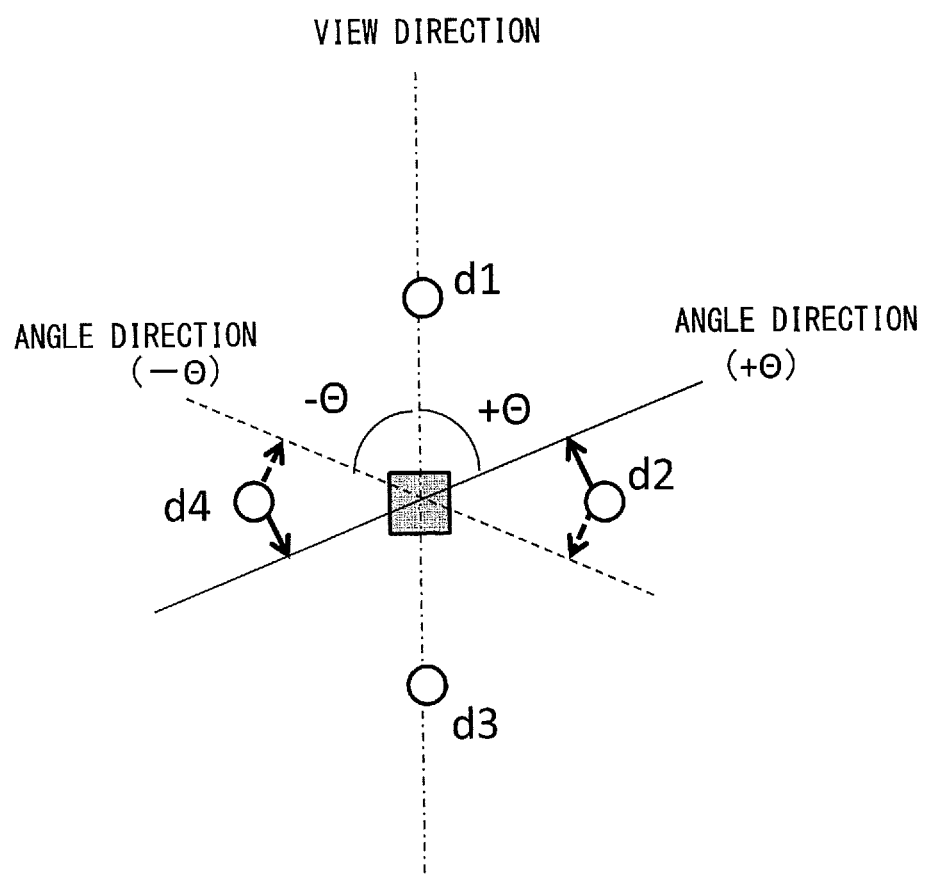
FIG. 10 illustrates a modification example 3 of the first embodiment.

As shown in FIG. 10, this modification example 3 is effective under the restriction that only four points are used, which are close to one another. In other words, when only the four points (d1 to d4) close to one another surrounding the deficient data are considered, the data to be used and its weight are equal in whichever the interpolation direction (angle) is, $+\Theta$ or $-\Theta$. For this case, if only a representative sinogram with the positive representative angle is prepared as the representative sinogram, it is possible to attend to whichever case; the angle of the point response trajectory is positive or negative.

Second Embodiment

The second embodiment additionally features that a representative sinogram is configured directly by a user.

Figure 11:
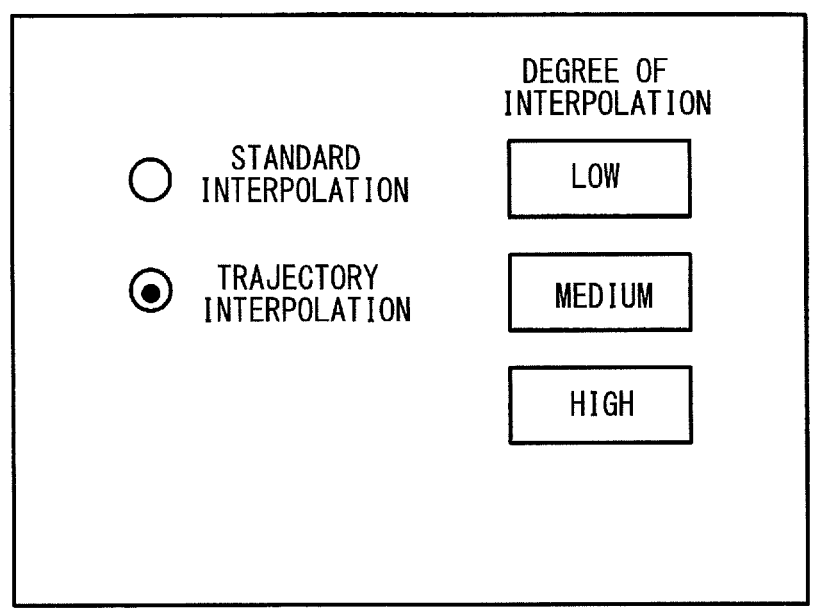
FIG. 11 illustrates one example of GUI according to the second embodiment.

FIG. 11 shows an example of GUI that is displayed on the input device 104. This is an example of GUI to designate a degree of the interpolation, selecting from "LOW", "MEDIUM", and "HIGH", and it is displayed, for instance, as a part of a menu for a user to select an image quality. When the degree of the interpolation is selected by the user, the number of representative sinograms is changed according to the degree of the interpolation thus selected.

The larger is the number of the representative sinograms, that is, the smaller is the increment of the angle of the representative sinograms being generated, the higher is the precision of the interpolation. Therefore, the degree of the interpolation is changed, in such a manner that the number of the representative sinograms becomes larger, along with changing from "LOW" to "MEDIUM", from "MEDIUM" to "HIGH".

For example, it is possible to configure such that channel interpolation is set as a default, which is a standard interpolation method, and the trajectory interpolation is performed when any of the interpolation degree above is selected. In the standard interpolation method, the sinograms can be interpolated uniformly. Therefore, the user can select more precise interpolation, after confirming the image obtained by the standard interpolation method.

Alternatively, the user may directly enter the number of the representative sinograms, the increment of the interpolation, and/or the maximum interpolation angle.

The X-ray imaging apparatus of the present invention has been described according to the embodiments which are mainly applied to the FFS. It should be noted that the present invention can be applied not only to the FFS, but also to projection data where deficient data is generated and thus interpolation is needed. In the drawings, there is illustrated a two-dimensional sinogram where the horizontal axis shows the channel direction, and the vertical axis shows the view direction. Alternatively, the sinogram may be two dimensional where the horizontal axis shows a slice direction and the vertical axis shows the view direction. It is also applicable to three-dimensional data including both axes in the channel direction and in the slice direction.

Numerical values shown in the aforementioned embodiments are just examples, and the present invention is not limited to those values.

INDUSTRIAL APPLICABILITY

According to the present invention, it is possible to implement data interpolation, which is close to the interpolation along a point response trajectory being an ideal interpolation method, together with reducing load on an arithmetic unit. Consequently, in a technique that needs interpolation of deficient data, such as FFS, a highly precise interpolation can be performed, thereby enhancing an image quality.

DESCRIPTION OF SYMBOLS

1 . . . X-ray tube, 2 . . . opening, 3 . . . subject, 4 . . . X-ray detector, 5 . . . bed, 8 . . . detector module, 9 . . . X-ray focus, 41 . . . X-ray detector element, 101 . . . recording device, 102 . . . arithmetic unit, 103 . . . control unit, 104 . . . input device, 105 . . . output device, 1021 . . . correction part, 1022 . . . fan-para converter, 1023 . . . data interpolation part, 1024 . . . image reconstruction part

What is claimed is:

1. An X-ray imaging apparatus comprising,
an X-ray source configured to generate X-rays from an X-ray focus,
an X-ray detector having a two-dimensional array of plural detector elements, configured to detect the X-rays emitted from the X-ray source and passing through a subject,
a rotary mechanism configured to rotate the X-ray source and the X-ray detector which are opposed to each other, and
an operation part configured to reconstruct a tomographic image of the subject, by using plural projection data items detected by the X-ray detector, according to emission of the X-rays from the X-ray source along with rotating an emitting direction of the X-rays, wherein,
the plural projection data items include a first sinogram where acquired data items are arranged, with a first axis representing detector element numbers in a rotation direction of the X-ray detector, and a second axis representing projection numbers respectively associated with rotation angles of the X-ray source, and
the operation part comprises a data interpolation part configured to interpolate the first sinogram, and an image reconstruction part configured to reconstruct an image by using a second sinogram that is generated by the data interpolation part,
the data interpolation part performs interpolation along various angles θ, in making up for data deficiency included in the first sinogram or in rearranging the data items in the form suitable for a reconstruction process, so as to generate plural second sinograms, and
the image reconstruction part performs an image reconstruction process including a process of weighted averaging of the plural second sinograms, using a weight corresponding to an angle difference between the angle θ and a slope of a trajectory on the second sinogram, depicted by a virtual point placed on a pixel position targeted for reconstruction.

2. The X-ray imaging apparatus according to claim 1, further comprising a control unit configured to control imaging, by switching a focal spot of the X-ray source to a plurality of positions, along with rotating the X-ray source.

3. The X-ray imaging apparatus according to claim 1, wherein,
the data interpolation part obtains the angle θ that is measured from the second axis of the first sinogram, and performs interpolation using weight in accordance with distance between a straight line along the angle θ passing through an interpolation target position, and data to be used for interpolation.

4. The X-ray imaging apparatus according to claim 1, wherein,
the interpolation along the angle θ is independent of a sign of the angle θ.

5. The X-ray imaging apparatus according to claim 1, wherein,
the data interpolation part imposes limitations on a maximum value and a minimum value of the angle θ, in accordance with the number of data sampling counts (the number of projection views) per rotation, and a position and a size of a display field of view or of a region of interest.

6. The X-ray imaging apparatus according to claim 1, wherein,
the data interpolation part determines the number of the second sinograms, in accordance with a user-selection of a reconstruction filter, a focus size, a rotation speed, a helical pitch, or smoothing intensity in an iterative reconstruction method.

7. The X-ray imaging apparatus according to claim 1, further comprising an input unit configured to input a processing condition of the operation part, wherein,
the data interpolation part determines the number of the second sinograms to be generated or a range of the angle θ, in accordance with the processing condition inputted via the input unit.

8. A method of reconstructing a tomographic image of a subject, by using a first sinogram where acquired data items are arranged, the data items being obtained by an X-ray imaging apparatus comprising an X-ray source, an X-ray detector, and a rotary mechanism, the first sinogram having a first axis representing detector element numbers arranged in the rotation direction of the X-ray detector, and the second axis representing projection numbers respectively associated with rotation angles of the X-ray source, comprising,
interpolating along various angles θ, in making up for data deficiency included in the first sinogram or in rearranging the data items in the form suitable for a reconstruction process, so as to generate plural second sinograms, and
weighted averaging of the plural second sinograms, using a weight corresponding to an angle difference between the angle θ and a slope of a trajectory on the second sinogram, depicted by a virtual point placed on a pixel position targeted for reconstruction.

* * * * *